US006143316A

United States Patent [19]

Hayden et al.

[11] Patent Number: 6,143,316

[45] Date of Patent: Nov. 7, 2000

[54] DIGESTIBLE POUCH AND METHOD FOR ADMINISTERING MEDICATIONS TO AN ANIMAL

[76] Inventors: Linda L. Hayden; Susan G. Foresman, both of 4061 Williams Rd., Estero, Fla. 33928

[21] Appl. No.: 08/709,000

[22] Filed: Sep. 6, 1996

[51] Int. Cl.$^7$ ................................ A61K 9/70; A61K 9/20

[52] U.S. Cl. .......................... 424/442; 424/438; 424/439; 424/451

[58] Field of Search .................................... 424/451, 439, 424/438, 469, 489, 442; 514/937, 962

[56] References Cited

U.S. PATENT DOCUMENTS

| | | | |
|---|---|---|---|
| 3,536,074 | 10/1970 | Aufhauser . | |
| 4,006,266 | 2/1977 | Bone et al. . | |
| 4,299,851 | 11/1981 | Lowe . | |
| 4,508,741 | 4/1985 | Corbett et al. . | |
| 4,857,333 | 8/1989 | Harold | 424/442 |
| 5,122,377 | 6/1992 | Miller et al. . | |
| 5,792,470 | 8/1998 | Baumgardner, Sr. | 424/442 |

*Primary Examiner*—Thurman K. Page
*Assistant Examiner*—R. Bawa
*Attorney, Agent, or Firm*—Laura G. Barrow

[57] ABSTRACT

A digestible pouch and method for aiding in the oral administration of substances suitable for ingestion, in particular medicinal agents, is disclosed. Specific embodiments of the invention include a pouch formed of an edible food stuff material that is pleasing to the recipient, wherein the pouch comprises an inner compartment area for housing the particular substance prior to oral administration. The inventive pouch is particularly useful in administering medications to common domestic animals and children to whom oral administration of such medications is often difficult.

20 Claims, 4 Drawing Sheets

DIGESTIBLE POUCH AND METHOD FOR ADMINISTERING MEDICATIONS TO AN ANIMAL

BACKGROUND OF INVENTION

1. Field of Invention

The present invention is related to a system for aiding in the oral administration of various substances, in particular medications, to animals.

2. Description of Related Art

A common problem encountered by many pet owners in treating a pet's illness or infection is the actual administration of the medication, especially via the oral route. Many animals refuse to take medication voluntarily due to the medication's unusual odor, taste, and/or texture. Often drastic, and consequently very difficult, measures must be taken to get the reluctant animal to take the medication, such as physically restraining the animal and forcing the medication down the animal's throat. Such methods are unpleasant for both the animal and the one having to administer the medication, the latter of whom may get scratched or bitten in the process. It is believed that the primary way of administering veterinary medications to reluctant animals via oral administration is by first embedding the medication in food, such as a piece of cheese, peanut butter, or meat (e.g. hot dog). Not only is this a messy process, especially with peanut butter, but there is a significant risk that the medication will fall out of the food. Furthermore, hiding the medication in a piece of food will generally only work for solid dosage forms. Liquid dosage forms are typically administered via an oral syringe, and thus there is no convenient way to "hide" the medication, including its taste and odor, prior to administration.

Similarly, children are often reluctant to take medications of any kind, and since many children are unable to swallow tablets or capsule whole, children must often be administered medications in liquid or chewable tablet forms. While much progress has been made in making pediatric medications more palatable, there are still some types that are notoriously bad-tasting. Thus, as with the veterinary administration of oral medications discussed above, there often ensues a wrestling match between the exasperated parent or care giver and the screaming child in attempting to administer the medication to the child. Moreover, since most pediatric medications are formulated in liquid dosage forms, it is often difficult to avoid spilling the medication from the measuring spoon. Further, even if one is successful initially getting the child to take the medication, it is likely the child will either spit the medication out or even vomit the medication, thus making compliance very difficult.

It is therefore desirable to have an oral delivery system that allows for the easy administration of medications to both pediatric and veterinary patients, wherein the delivery system ensures that the total dose is delivered without being lost prior to administration, is edible, and has an acceptable texture as well as a pleasant taste and odor so as to mask the odor and/or taste of the medication contained therein.

SUMMARY OF INVENTION

The present invention is directed to a delivery system and method, especially a pharmaceutical delivery system, which is particularly useful in aiding in the oral administration of medications, in particular medications that are difficult to administer due to their unpleasant odor or taste. The present invention is especially useful in administering pediatric and veterinary medications, since these patients are particularly sensitive to the taste and odor of medications and often will refuse to take any or all of the medication.

Certain aspects of the present invention comprise a pouch having a closed bottom end, at least two sides, and an open top end, all of which define an inner compartment wherein an oral medication or any other substance suitable for ingestion may be inserted. Preferably, the material used to construct the pouch is formed of a firm yet flexible material such that upon placement of the medication within the pouch's compartment, the top ends of the pouch may be sealed together, for example, to enclose completely the oral medication therein and thus prevent loss of the medication prior to administration. Alternatively, the pouch may be formed of a rigid food material. After the medication has been placed in the pouch, the pouch may be administered orally to the patient.

Since the pouch is ingested by the patient, the material used to the construct the pouch must be made of an edible material, preferably one comprising at least one food stuff selected from the group consisting of dairy products, meat products, wheat, corn, soybean, and the like. It is also preferable that the material be pleasant smelling and tasting so as to mask any unpleasant odor/taste of the medication contained therein.

DETAILED DESCRIPTION OF THE PREFERRED EMBODIMENTS

The present invention is directed to a digestible pouch and method particularly useful in aiding in the oral administration of medications, in particular medications that are difficult to administer orally due to the medication's unpleasant odor or taste. The inventive pouch may be administered to any animal, such as mammals (including humans), reptiles, and birds, and is particularly advantageous for use in children and common domestic animals, especially dogs and cats.

Figure 1:
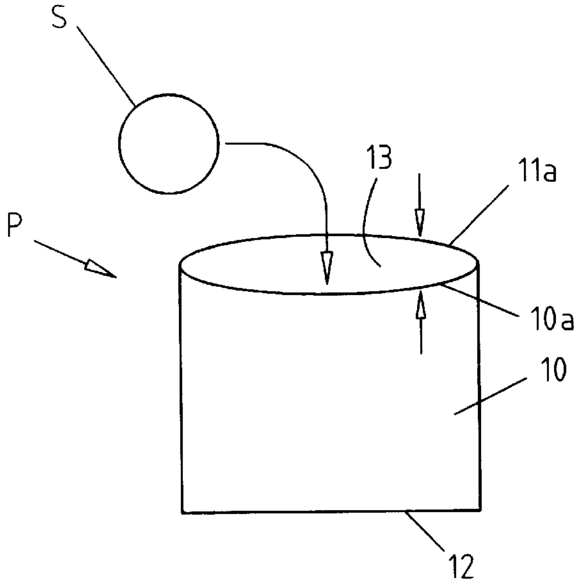
FIGS. 1–2 are elevated views of one embodiment of the inventive delivery system.
Figure 2:
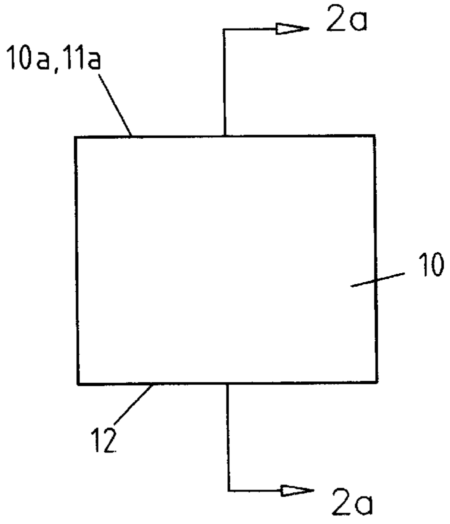
Figure 2A:
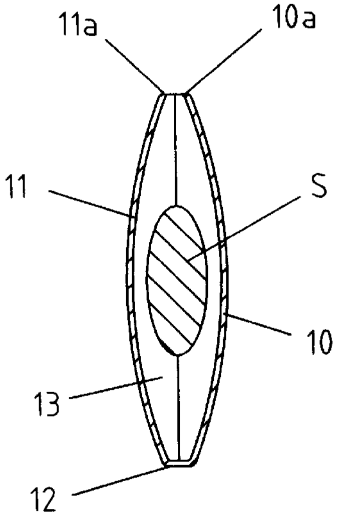
FIG. 2*a* is a cross-section of the delivery system taken along lines 2*a*—2*a*.
Figure 3:
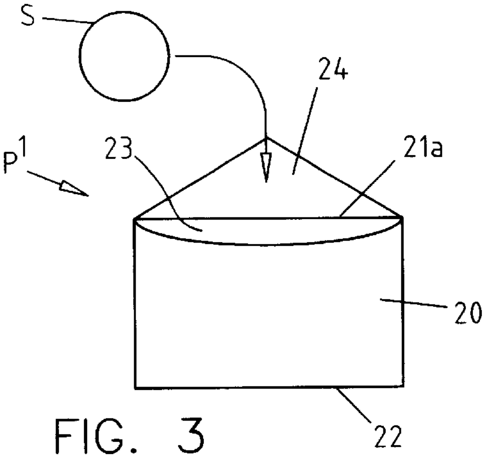
FIGS. 3–6 are elevated views of a second embodiment of the inventive delivery system.
Figure 4:
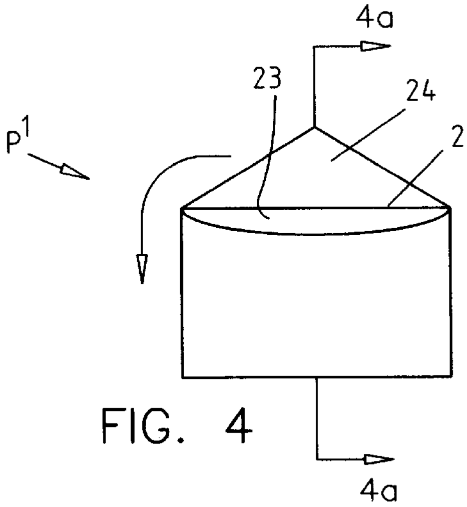

Referring now to the figures, the inventive pouch (P) may be of any size and configuration, including a square or rectangle, as shown in the figures. As shown in FIGS. 1–2 and 2*a*, the pouch (P) may include at least two side walls (10, 11) and a lower end (12) which together define an inner compartment (13) for housing a substance (S) suitable for ingestion, preferably a medicinal agent. In this embodiment, after the substance (S) is placed within the pouch, the top edges (10*a*, 11*a*) of the pouch may be pressed together in the direction of the arrows, thereby sealing the substance therein to prevent the substance from falling out of the pouch's inner compartment (13) prior to, and during, the administration of the system to the animal.

In the foregoing embodiment as well as the other embodiments discussed in more detail below, the preferred material used to form the pouch is a food stuff of the type typically given to, or acceptable to, the particular patient (e.g. veterinary or pediatric patients). In veterinary applications, suitable food materials are those commonly known by those of ordinary skill in the art, such as meats and meat by-products, dairy products, animal fat, soybean, corn, wheat, etc., and combinations thereof. These materials are generally employed in current food preparations for non-human animals, such as dogs and cats, for example. It is preferable that the consistency of the material(s) used in fabricating the pouch be sufficiently pliable, especially when it is desirable that the ends (10*a*, 11*a*) are to be sealed together (i.e. the material is capable of adhering or sticking onto itself upon the application of sufficient force), as discussed above. For pediatric use, a suitable material includes sticky, flexible candy, such as that used in FRUIT ROLL UPS (distributed by General Mills, Inc., Minneapolis, Minn.), for example, which comprises of concentrated fruit, sugar, maltodextrin, corn syrup, and cottonseed oil. It is also preferable that the consistency of the material be such that the pouch, while being sufficiently pliable as discussed above, be sufficiently firm so as to maintain its shape, in particular with respect to the inner compartment, so that the substance contained therein may easily be inserted into the compartment without destroying the integrity of the pouch.

Figure 5:
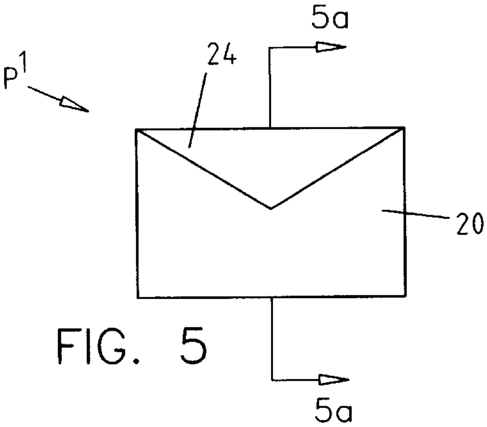
Figure 6:
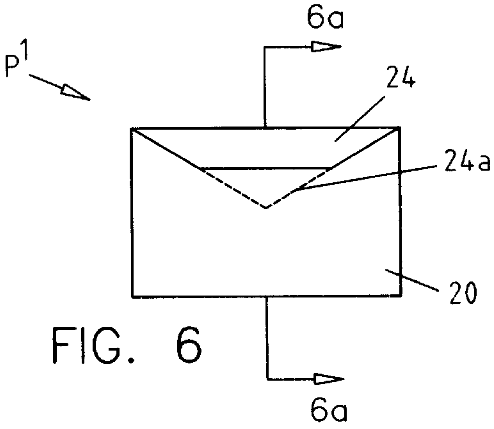
Figure 4A:
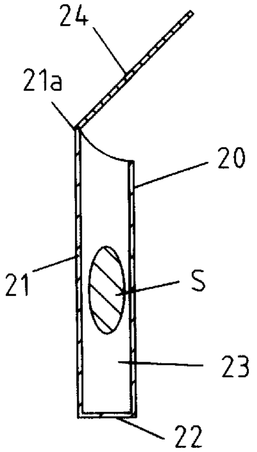
FIG. 4*a* is a cross-section of the delivery system illustrated in FIG. 4 taken along lines 4*a*—4*a*.
Figure 5A:
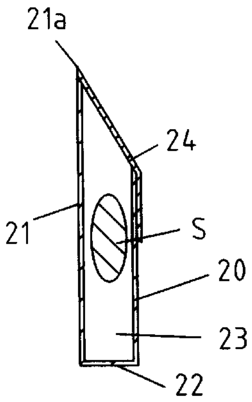
FIG. 5*a* is a cross-section of the delivery system illustrated in FIG. 5 taken along lines 5*a*—5*a*.
Figure 6A:
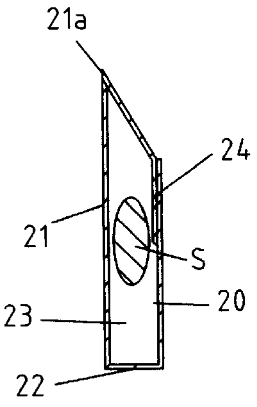
FIG. 6*a* is a cross-section of the delivery system illustrated in FIG. 6 taken along lines 6*a*—6*a*.

FIGS. 3, 4–4*a*, 5–5*a*, and 6–6*a* illustrate another embodiment of the present invention wherein the pouch ($P^1$) comprises a lower end (22) and two side walls (20, 21), which in combination define an inner compartment (23), as well as a flap (24) integral with a top edge (21*a*) of one of the side walls (21). After the substance is inserted into the compartment (23), the flap (24) is pulled downward in the direction of the arrows (FIG. 4) and over the top edge of the opposite side wall to enclose completely the substance (S) within the pouch ($P^1$) to prevent it from falling out prior to and during oral administration. The flap (24) may be positioned along the outer surface of the opposite side wall (20) and most preferably is adhered to the opposite side wall (20) by applying simple pressure between the flap (24) and the outer surface of the side wall (20), thereby "sealing" the substance therein (FIGS. 5–5*a*). Alternatively, after the flap (24) is folded downward as discussed above, a portion (24*a*) of the flap, (depicted in ghost lines) may be inserted into the pouch such that the flat is in contact with the inner surface of the opposite side wall (20), as shown in FIGS. 6 and 6*a*.

Figure 9:
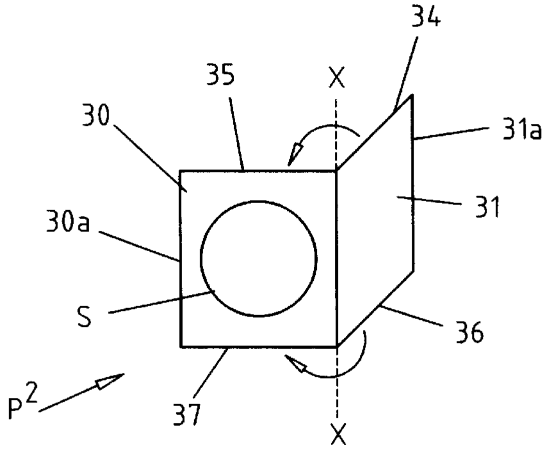
Figure 10:
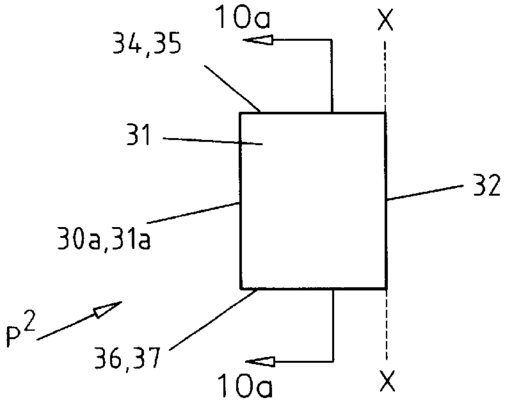
Figure 10A:
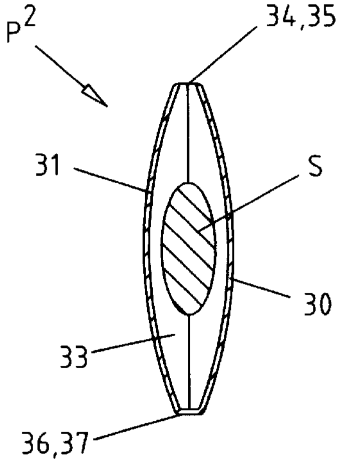
FIG. 10*a* is a cross-section of the pouch illustrated in FIG. 10 taken along lines 10*a*—10*a*.

In a third embodiment, as shown in FIGS. 7–10, and 10*a*, the pouch ($P^2$) is a flat sheet having a top surface (3) and a center axis (X) defining two adjacent regions (30, 31) on the top surface (3). The substance (S) is placed on one region (30) of the sheet, as shown in FIG. 9, after which the sheet is folded in half along the center axis (X) in the direction of the arrows to form a pouch ($P^2$) comprising the inner compartment (33) and lower end (32). All of the edges (30*a*, 31*a*, and 34–37) are sealed together, preferably by applying pressure along all of the edges (i.e. edge 30*a* to edge 31*a*, edge 34 to edge 35, and edge 36 to edge 37) to enclose completely the substance (S) therein.

Figure 7:
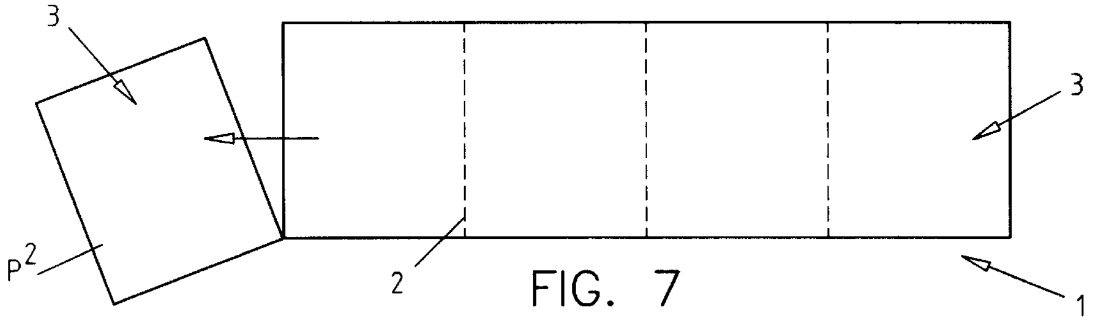
FIG. 7 is an elevated view of a third embodiment of the inventive delivery system, wherein five pouches are connected to each other in the form of a strip.
Figure 8:
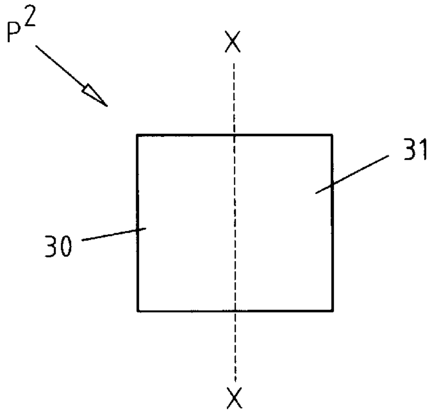
FIGS. 8–10 are elevated views of a single pouch of the delivery system illustrated in FIG. 7.
Figure 11:
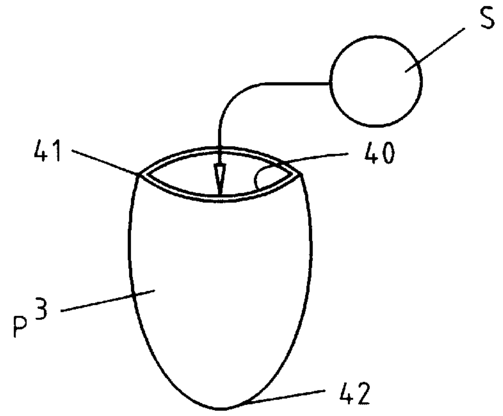
FIG. 11 is an elevated view of a fourth embodiment of the present invention.
Figure 11A:
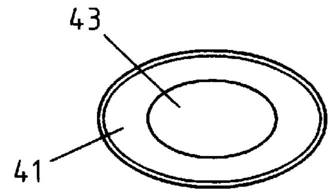
FIG. 11*a* is a top plan view of the embodiment illustrated in FIG. 11.
Figure 12:
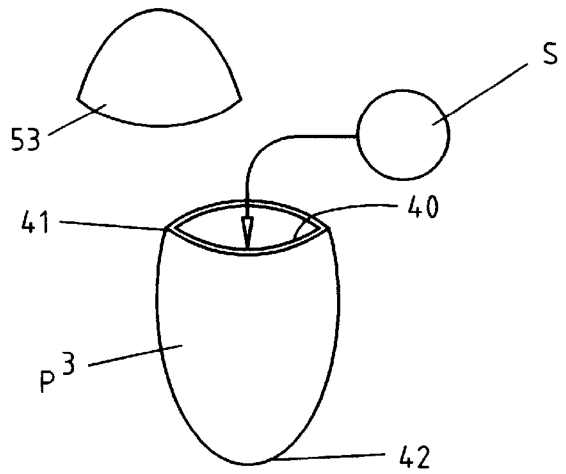
FIG. 12 is an exploded view of the embodiment shown in FIG. 11 wherein the system further includes a cap.

The inventive pouches may also be supplied commercially in strips comprising more than one sheet, wherein the strip (1) comprises a series of perforations (2) separating each sheet, as shown in FIG. 7. When desired, an individual sheet may be removed along the perforations as shown. FIGS. 11–11*a* and 12 illustrate another embodiment of the present invention wherein the pouch ($P^3$) has an egg-like configuration and comprises an inner compartment (40) for housing a substance (S) suitable for ingestion. The pouch ($P^3$) has a closed bottom end (42) and an open top end (41) communicating with the inner compartment (40), as shown in FIG. 11, for example. The pouch is formed of an food stuff like the other embodiments described herein and similarly, the food stuff may be somewhat flexible. However, a more preferred food stuff for use in this particular embodiment is one that is substantially rigid to form a pouch having a fixed configuration. In veterinary applications, a preferred food stuff comprises any of the food stuffs and combinations thereof typically used in dry food products for domestic animals. Exemplary products include, but are not limited to, SCIENCE DIET (vended by Hill's Pet Nutrition, Inc., Topeka, Kans.), and PURINA DOG CHOW and PURINA CAT CHOW (vended by Ralston Purina Company, St. Louis, Mo.). FIGS. 11 and 11*a* illustrate one version of this embodiment whereby after the substance(s) is placed within the inner compartment (40), a plug (43) having a semi-solid consistency and preferably comprising a palatable food stuff material is inserted within the compartment over the substance(s) to enclose completely the substance(s) therein. Preferable materials include, but are not limited to, processed cheese (e.g. CHEESE WHIZ, vended by Kraft, Inc., Glenview, Ill.), peanut butter, cream cheese, and various meat products.

Figure 12A:
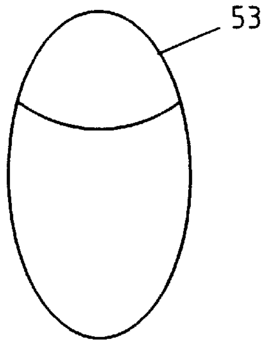
FIG. 12*a* is an elevated view of the delivery system shown in FIG. 12.
Figure 13:
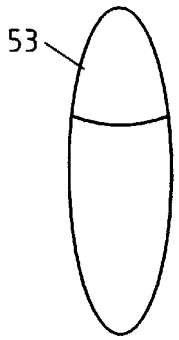
FIG. 13 is an elevated view of a similar embodiment shown in FIG. 12, wherein the assembled delivery system is narrower than that shown in FIG. 12.

FIGS. 12–12*a* illustrate a slightly modified version of the embodiment shown in FIGS. 11 and 11*a*, whereby instead of a plug (43), the system includes a pre-formed cap (53) that fits onto the top end (41) of the pouch ($P^3$) to enclose the substance (S) therein. Preferably, the cap (53) is formed of the same substantially rigid, edible material as discussed above for the pouch ($P^3$). FIG. 13 illustrates a similar embodiment as shown in FIGS. 12–12*a*, wherein the combined system (i.e. combination pouch and cap) has a relatively narrower, "bullet-like" configuration.

The embodiments illustrated in FIGS. 11–11*a*, 12–12*a*, and 13 may be of any size or configuration in addition to those shown herein. Since these embodiments are preferably formed of the same material as dry animal food, a preferred way of administering these particular pouches is to mix them directly with the animal's food. Thus, it is preferable that the size and shape of the pouch be similar to that of the animal's particular food.

While the foregoing embodiments of the inventive pouch are preferred, it will be recognized by those of ordinary skill in the art that obvious modifications of the size and configuration of the pouch in all embodiments of the inventive digestible pouch and method are well within the scope of the present invention, provided that in any embodiment or modification thereof there exists a compartment wherein the medication or substance may be contained prior to administration.

It is further desirable that the food stuff(s) used in forming the pouch have a pleasant odor and taste or include odor/taste masking agents to render the substance(s) contained within the pouch more palatable. Moreover, especially in veterinary applications, it may be desirable that the food stuff used to form the pouch have a texture similar to conventional animal "snacks" in order to improve upon the palatability of the product.

The inventive pouch is particularly advantageous in aiding in the administration of a medicinal agent comprising at least one pharmacologically active agent formulated in a pharmaceutical dosage form suitable for oral administration. Exemplary pharmacological agents include, but are not limited to, antibiotics (e.g. antibacterial, antiviral, antifungal, and antihelminic agents), vitamins and minerals, cardiovascular agents, neurological agents, and the like which are generally administered to humans and other animals. Suitable pharmaceutical oral dosage forms include, but are not limited to, the conventional forms such as tablets, capsules, solutions, elixirs, suspensions, pills, and the like. In addition, the substance(s) could be of a non-medicinal type, such as a particular food stuff, for example.

In some cases, it may be desirable to administer more than one medication to the patient simultaneously. Here, the pouch should be large enough to contain more than one medication or substance. Alternatively, the pouch could be used to house both a medication, for example, plus a smaller second pouch containing a second medication or substance, for example.

What is claimed is:

1. A method of orally administering medical agents to an animal, said method comprising:

(a) introducing at least one medicinal agent into an inner compartment of a pouch, said at least one medicinal agent formulated in a pharmaceutically acceptable dosage form for oral administration, and wherein said pouch is formed of a food stuff and comprises first and second opposing side walls, each of said side walls having an outer surface, an inner surface, and a top edge, wherein said pouch further includes a flap integral with the top edge of said first side walls;

(b) folding down said flap to enclose said at least one medicinal agent within said pouch; and (c) orally administering said pouch containing said at least one medicinal agent to an animal for ingestion.

2. The method of claim 1, wherein said animal is a domestic animal selected from the group consisting of dogs and cats.

3. The method of claim 1, wherein said animal is a human.

4. The method of claim 1, wherein said step of folding down said flap includes folding said flap over the top edge of said second side wall and onto said outer surface of said second side wall of said pouch to enclose said least one medicinal agent within said pouch.

5. The method of claim 4, wherein said animal is a domestic animal selected from the group consisting of dogs and cats.

6. The method of claim 4, wherein said animal is a human.

7. The method of claim 1, wherein said step of folding down said flap includes inserting a portion of said flap into said compartment such that said flap is in contact with the inner surface of said second side wall to enclose said at least one medicinal agent within said pouch.

8. The method of claim 7, wherein said animal is a domestic animal selected from the group consisting of dogs and cats.

9. The method of claim 7, wherein said animal is a human.

10. A method of orally administering medicinal agents to an animal, the method comprising:

(a) removing a first flat sheet formed of a food stuff from a strip comprising a series of flat sheets removably joined to one another by a perforated edge, wherein said first flat sheet and each of said series of flat sheets include outer edges, a top surface, and a center axis defining two adjacent regions on said top surface;

(b) placing at least one medicinal agent onto one of said regions of said top surface of said first flat sheet, wherein said medicinal agent is formulated in a pharmaceutically acceptable dosage form for oral administration, (c) folding said first flat sheet along said center axis of said first flat sheet and sealing said outer edges of said first flat sheet to form a pouch comprising an inner compartment between said regions of said first flat sheet, wherein said at least one medicinal agent is scaled therein; and (d) orally administering said pouch containing said at least one medicinal agent to an animal for ingestion.

11. The method of claim 10 wherein said animal is a domestic animal selected from the group consisting of dogs and cats.

12. The method of claim 10, wherein said animal is a human.

13. A method for orally administering medicinal agents to an animal, the method comprising:

(a) introducing at least one medicinal agent into an inner compartment of a pouch, said at least one medicinal agent formulated in a pharmaceutically acceptable dosage form for oral administration, and wherein said pouch is formed of a food stuff and comprises a closed bottom end, outer sides integral with said bottom end to define said inner compartment, and an open top end in communication with said inner compartment, (b) securing a substantially rigid cap over said top end of said pouch to enclose said at least one medicinal agent therein, said cap formed of a food stuff; and (c) orally administering said pouch containing said at least one medicinal agent to an animal for ingestion.

14. The method of claim 13, wherein said animal is a domestic animal selected from the group consisting of dogs and cats.

15. The method of claim 13, wherein said animal is a human.

16. The method of claim 13, wherein said pouch in combination with said cap has a substantially oval configuration.

17. A method for orally administering medicinal agents to an animal, the method comprising:

(a) introducing at least one medicinal agent into an inner compartment of a pouch, said at least one medicinal agent formulated in a pharmaceutically acceptable dosage form for oral administration, and wherein said pouch is formed of a food stuff and comprises a closed bottom end, outer sides integral with said bottom end to define said inner compartment, and an open top end in communication with said inner compartment;

(b) inserting a plug through said top end of said pouch and within said compartment over said at least one medicinal agent to enclose said at least one medicinal agent therein, said plug formed of a semi-solid food stuff; and (c) orally administering said pouch containing said at least one medicinal agent to an animal for ingestion.

18. The method of claim 17, wherein said animal is a domestic animal selected from the group consisting of dogs and cats.

19. The method of claim 17, wherein said animal is a human.

20. The method of claim 17, wherein said pouch in combination with said plug has a substantially oval configuration.

* * * * *